(12) United States Patent
Hardikar et al.

(10) Patent No.: US 8,251,576 B1
(45) Date of Patent: Aug. 28, 2012

(54) COLD LIFT-OFF TEST FOR STRENGTH OF FILM STACK SUBJECTED TO THERMAL LOADING

(75) Inventors: Kedar Hardikar, San Jose, CA (US); Todd Krajewski, Mountain View, CA (US)

(73) Assignee: Mia Sole, Santa Clara, CA (US)

( * ) Notice: Subject to any disclaimer, the term of this patent is extended or adjusted under 35 U.S.C. 154(b) by 678 days.

(21) Appl. No.: 12/455,398

(22) Filed: May 30, 2009

(51) Int. Cl.
  *H01L 31/0203* (2006.01)
  *H02K 6/00* (2006.01)
  *G01N 25/32* (2006.01)
  *G01N 25/58* (2006.01)
  *G01N 3/18* (2006.01)

(52) U.S. Cl. ............ 374/5; 374/57; 374/121; 320/101; 324/671.1; 136/290; 136/206

(58) Field of Classification Search .......... 324/500, 324/750.01, 756.01, 761.01, 501; 320/101, 320/FOR. 134; 382/141; 136/290, 206, 136/210, 243, 251, 252; 374/4, 5, 57, 100, 374/141, 120, 121, 137, 166, 167, 110, 112, 374/115, 30, 43–45; 340/636.1, 636.2
See application file for complete search history.

(56) References Cited

U.S. PATENT DOCUMENTS

| | | | |
|---|---|---|---|
| 4,080,221 A * | 3/1978 | Manelas | 136/248 |
| 4,097,308 A | 6/1978 | Klein | |
| 4,217,180 A | 8/1980 | Baxter | |
| 4,612,805 A | 9/1986 | Bruce | |
| 5,240,546 A | 8/1993 | Shiga | |
| 5,334,844 A | 8/1994 | Pollard | |
| 5,367,174 A * | 11/1994 | Bazile et al. | 250/559.45 |
| 5,410,162 A | 4/1995 | Tigelaar | |
| 5,980,103 A | 11/1999 | Ikuno | |
| 6,113,262 A | 9/2000 | Purola | |
| 6,604,853 B2 | 8/2003 | Chao | |
| 6,974,976 B2 | 12/2005 | Hollars | |
| 7,173,179 B2 * | 2/2007 | Nicoletti et al. | 136/246 |
| 8,138,782 B2 * | 3/2012 | Elgar et al. | 324/761.01 |
| 2003/0063006 A1 * | 4/2003 | Gutta et al. | 340/603 |
| 2003/0063008 A1 * | 4/2003 | Kobayashi et al. | 340/635 |
| 2007/0283996 A1 | 12/2007 | Hachtmann | |
| 2008/0053519 A1 | 3/2008 | Pearce | |
| 2009/0179651 A1 * | 7/2009 | Elgar et al. | 324/501 |
| 2010/0046575 A1 * | 2/2010 | Hebert et al. | 374/57 |
| 2010/0197051 A1 * | 8/2010 | Schlezinger et al. | 438/16 |
| 2011/0132437 A1 * | 6/2011 | Kost et al. | 136/251 |
| 2011/0177648 A1 * | 7/2011 | Tanner et al. | 438/72 |
| 2011/0314672 A1 * | 12/2011 | Lu et al. | 29/879 |

* cited by examiner

*Primary Examiner* — Gail Verbitsky
(74) *Attorney, Agent, or Firm* — Cascio & Zervas (57) ABSTRACT

Multilayer articles such as thin-film solar cells can be effectively tested under thermal load in a mini-module that includes a chamber or enclosure in which one or more laminated multilayer articles are housed. The inner dimensions of the chamber, at least along the axis that is perpendicular to the plane defined by the laminated solar cells, are configured to remain substantially constant during testing. Cooling the laminated solar cells in the mini-module device causes the encapsulant material to shrink and thereby induces accelerated failures in the laminated solar cells and associated structures. A technique of detecting the presence of defects or failures is near infrared radiation thermography wherein NIR images of the laminated solar cells are taken during the cooling process. The color patterns manifested from the cooled laminated solar cells can reveal the location, nature and extent of the defect or failure.

6 Claims, 7 Drawing Sheets

COLD LIFT-OFF TEST FOR STRENGTH OF FILM STACK SUBJECTED TO THERMAL LOADING

FIELD OF THE INVENTION

The present invention generally relates to an accelerated test to determine the structural integrity of film stacks and more particularly to techniques to detect and gauge the physical behavior of laminated thin-film photovoltaic or solar cells as they are subjected to a cooling protocol.

BACKGROUND OF THE INVENTION

Photovoltaic cells are widely used in residential structures and roofing materials for generation of electricity. A plurality of photovoltaic cells are interconnected in series or in parallel and are integrated with residential structures such as roofing slates, roofing tiles, building claddings and the like. Interest in thin-film photovoltaics has expanded in recent years. This is due primarily to improvements in conversion efficiency of cells made at the laboratory scale, and the anticipation that manufacturing costs can be significantly reduced compared to the older and more expensive crystalline and polycrystalline silicon technology. The term "thin-film" typically refers to the thickness of the photovoltaic p-n junction layers and is used to distinguish this type of solar cell from the more common silicon based cell, which uses a relatively thick silicon wafer. For example, CIGS or CdTe are classes of "thin film" photovoltaic structures (usually less than 10 microns in total thickness). Although these photovoltaic structures can be deposited onto thick, heavy stainless steel or even onto glass, solar cells fabricated in this manner are still considered "thin film" solar cells. In operation, a number of thin-film solar cells are electrically connected to each other and mounted in a support structure or frame called a photovoltaic module. The module is enclosed within a protective panel.

Various transparent encapsulants, such as organic polymers, are used for encapsulating the photovoltaic cell to prevent the incursion of moisture into the photovoltaic cell. A copolymer of ethylene and vinyl acetate (ethylene vinyl acetate (EVA)) is a commonly used polymeric material for encapsulating the photovoltaic cells.

Mechanical tests such as the commonly referred to "peel test" are currently used to quantify the strengths of film stacks that form solar cells. The test parameters employed in these test protocols do not simulate the actual operating conditions of the solar cells and therefore do not yield sufficiently accurate information regarding the solar cells' true behavior over its expected commercial operational lifetime.

SUMMARY OF THE INVENTION

The present invention is based in part on the demonstration that multilayer articles can be effectively tested under thermal load in a mini-module that includes a chamber or enclosure in which one or more laminated multilayer articles are housed. The inner dimensions of the chamber or enclosure, at least along the axis that is perpendicular to the plane defined by the laminated multilayer articles, are configured to remain substantially constant during testing. The mini-modules of the present invention are particularly suited for testing thin-film solar cells, individual components thereof such as the encapsulant material, e.g., EVA, as well as other components or structures that form commercial solar modules, such as laminated busbars and laminated conductor wires.

In one aspect, the invention is directed to a thermal strength test for a multilayer article that includes the steps of:

positioning the multilayer article within a chamber having defined inner dimensions;

laminating the multilayer article within the chamber with an encapsulant;

cooling the laminated multilayer article to a predetermined temperature wherein the inner dimensions of the chamber, at least along an axis that is perpendicular to a plane defined by the multilayer article, remain substantially constant during cooling; and detecting the presence of defects in the laminated multilayer article.

In another aspect, the invention is directed to a method of testing a solar cell that includes the steps of:

positioning the solar cell within a chamber having defined inner dimensions;

laminating the solar cell with an encapsulant that is added to the chamber;

cooling the laminated solar cell to a temperature sufficient to cause defects to appear wherein the inner dimensions of the chamber, at least along an axis that is perpendicular to a plane defined by the solar cell, remain substantially constant during cooling; and detecting the presence of defects in the solar cell.

In yet another aspect, the invention is directed to a thermal strength test assembly for testing a multilayer article that includes:

a housing defining a chamber into which the multilayer article is mounted and laminated;

means for cooling the laminated multilayer article to a temperature sufficient to cause defects to appear wherein chamber is configured so that the inner dimensions of the chamber, at least along an axis that is perpendicular to a plane defined by the multilayer article, remain substantially constant during cooling; and means for detecting the presence of defects in the laminated multilayer article.

A preferred technique of detecting the presence of defects or failures is near infrared radiation thermography wherein NIR images of the laminated multilayer articles, such as solar cells, are taken and compared to NIR images that are taken at ambient temperatures. The contrast in color manifesting from the cooled multilayer articles can reveal the location, nature and extent of the defects or failures.

BRIEF DESCRIPTION OF THE DRAWINGS

FIGS. 7A and 8B are scanning electron microscope (SEM) images of cross sectional views of a solar cell that was subject to cooling in a mini-module;

DETAILED DESCRIPTION OF PREFERRED EMBODIMENTS

The present invention is directed to accelerated techniques for gauging the strengths of a multilayer structure by measuring its response to a controlled thermal cycle. Multilayer structures typically comprise a multilayer stack that is formed on a substrate. The invention is particularly suited for testing multilayer thin-film stacks that comprise different materials such as metals and dielectrics and wherein the thickness of the films varies such as in semiconductor devices. While the accelerated test will be illustrated in measuring the structural integrity of solar cells, it is understood that the test is applicable to other multilayer structures as well.

Figure 1A:
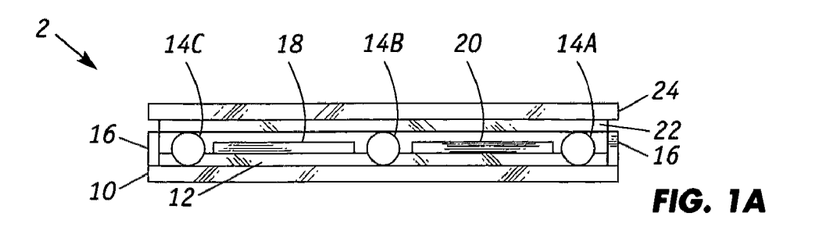
FIG. 1A is a cross sectional view of a pre-assembled mini-module depicting the components prior to undergoing thermal, compressive lamination.
Figure 1B:
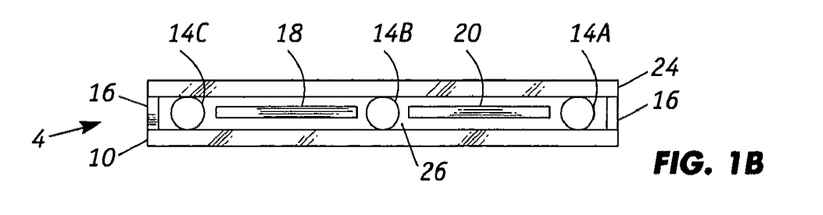
FIG. 1B is a cross sectional view of the mini-module that is formed after lamination.

Photovoltaic or solar cells to be tested are laminated and incorporated into a mini-module as shown in FIGS. 1A and 1B. As illustrated in FIG. 1A, the mini-module is prepared by first arranging the components thereof into a vertical stack assembly 2 wherein a first layer 12 of transparent encapsulant material is positioned over the planar surface of lower transparent substrate 10. Layer 12 includes crater-shaped apertures that are formed with a soldering iron operating at low temperate; in this arrangement, each of the plurality of spacers 14A, 14B, and 14C is positioned in an aperture. A hard plastic template, with an aperture pattern therein, can be used as a guide in forming the apertures in layer 12. Dual solar cells 18, 20 are then placed on the surface of encapsulant layer 12 with each solar cell being positioned between two spacers. A strip of solar edge tape 16 is secured around the outer perimeter of the spacers 14A and 14C. A second encapsulant layer 22 is placed onto and is supported by the plurality of spacers and finally an upper transparent substrate 24 is placed over encapsulant layer 22.

Vertical stack assembly 2 is then heated to a temperature sufficient to melt the materials that form encapsulant layers 12, 22. Depending on the particular encapsulant material used, assembly 2 is typically heated to about 150 to 180° C. for about 4 to 8 minutes and preferably under vacuum. As the encapsulant material melts, a compressive force is also applied to stack assembly 2 so that the encapsulant material completely fills the open region created by the plurality of spacers as the encapsulant layers 12 and 22 blend together to laminate solar cells 18, 20. After the heating process, the encapsulant material is allowed to cool to ambient temperatures whereby mini-module 4 forms, as shown in FIG. 1B, with a single laminant layer 26 solidly enclosing solar cells 18, 20.

Figure 1C:
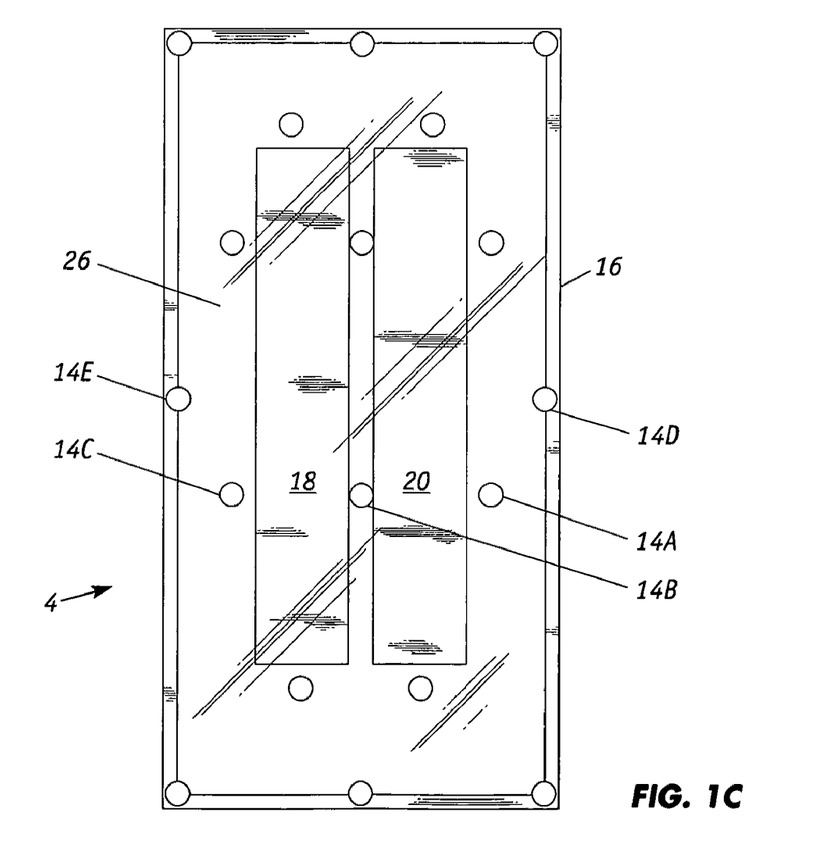
FIG. 1C is a top plan view of the mini-module.

As shown in FIG. 1C, besides spacers 14A, 14B and 14C, additional spacers including spacers 14D, 14E, 14F etc. are distributed strategically around the solar cells in mini-module 4. The spacers serve to maintain the vertical distance between transparent substrates 10, 24 (FIG. 1B). Thus, the vertical dimension (or height) of the enclosure which is perpendicular to the plane defined by the solar cells remains constant; the spacers also keep edge tape 16 stationary at the perimeter of mini module 4 however since the spacers are not permanently attached to the lower or upper substrates, solar edge tape 16 may contract if it adheres to laminant layer 26. In this fashion, the inner dimensions of the chamber or cell as defined by the inner surfaces of transparent substrates 10, 24 and edge tape 16 remain substantially constant during the cooling process as described herein.

The transparent substrates can be made of any suitable material that can withstand the heating and compressive force used in forming the mini-modules and the cooling protocol during the testing as described herein. A preferred material is stippled tempered glass that is about 3 mm thick. The spacers can be made of suitable solid material such as metal, e.g., stainless steel, or ceramics, e.g., zirconia oxide. The diameters of the spacers are preferably the same and their diameters must be larger than the thickness of the solar cells being tested. For thin-film solar cells that typically have thickness of 0.001 mm to 0.075 mm, the spacers typically have a thickness of about 0.7 mm to 1.2 mm. Preferred spacers comprise spheres or beads having a diameter of approximately 1.0 mm. The encapsulant layers 12 and 22 (FIG. 1A) are typically each about 0.50 mm to 0.65 mm thick.

It has been demonstrated that cooling mini-module 4 of FIGS. 1B and 1C under a prescribed regiment accelerates the rate at which structural defects in the laminated solar cells manifests themselves. Since the separation between the two substrates 10, 24 is determined by the size of the spacers so that the distance between the two substrates is held constant, laminant layer 26 is constrained. Stiffening of laminant layer 26 at low temperatures and its subsequent shrinkage due to its high coefficient of thermal expansion (CTE) introduces failures to the solar cell at its weakest interface as laminant layer 32 lifts off from the surfaces of substrates 10, 24. A preferred technique of detecting the locations of solar cell failures is NIR thermography. In addition, solar cell failures, especially those that involve external components of the solar cells and not the internal layers of the cell stack, can often be observed directly with the unaided eye in the form of color changes as the structural integrity of the solar cell is compromised. Thus, the location in a solar cell where failure has occurred can be detected by changes in the hue of the reflected light from the solar cell or other solar cell structures or components.

Figure 2:
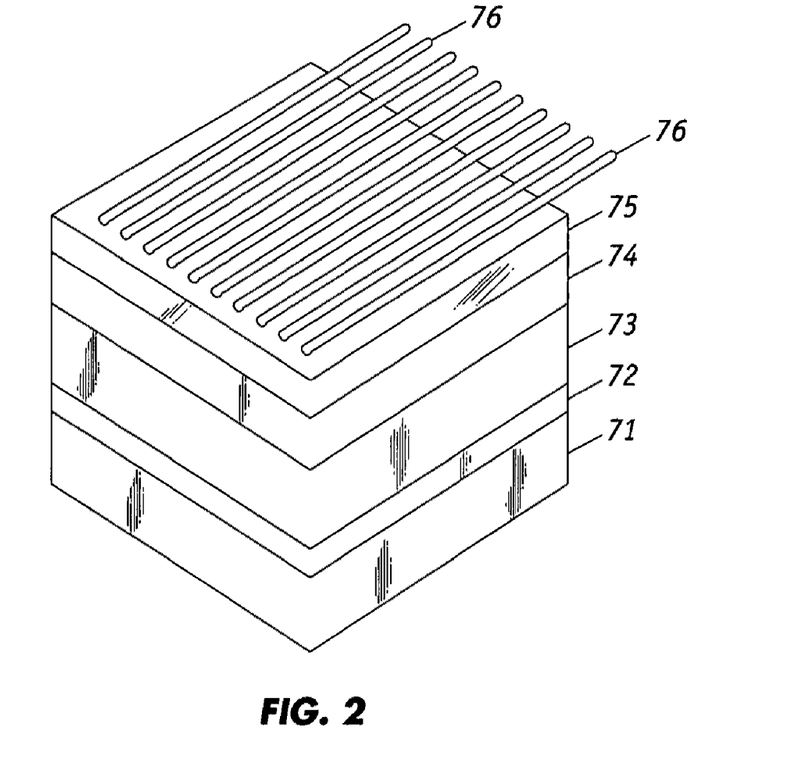
FIG. 2 is a perspective view of a representative solar cell structure.

The mini-module devices of the present invention are particularly suited for testing thin-film solar cells that are described, for example, in U.S. Pat. No. 6,974,976 to Hollars, which is incorporated herein by reference. As shown in FIG. 2, a preferred thin-film solar cell stack includes a flexible substrate 71, a bottom contact layer comprising a molybdenum conductive film 72, a p-type semiconductor consisting of copper, indium, gallium and selenium (CIGS) absorber layer 73, buffer or adhesive layer 74, and a transparent electrically conductive top contact layer 75. Solar cells are typically assembled into modules with each module including a plurality of electrically interconnected solar cells. An interconnect, that comprises an electrically insulating carrier and at least one electrical conductor, can be employed to connect the solar cells within the module. As shown in FIG. 2, conductors can comprise a plurality of wires 76 that are in electrical contact with a major portion of a surface of top contact layer 75 which functions as a first polarity electrode of a first solar cell to collect current from the solar cell. The wires 76 would also electrically connect a portion of a second (or opposite) polarity electrode of a second solar cell (not shown) of the module. As further described herein, to test the electrical contact characteristics of the bottom and top contact layers 72, 75, a busbar can be connected to each layer before the solar cell is laminated in a mini-module. Photovoltaic modules are described, for example, U.S. Patent Application 2007/0283996 to Hachtmann et al. and 2009/0014057 to Croft et al., which are both incorporated herein by reference. Finally, laminated photovoltaic cells are described, for example, in U.S. Patent Application 2008/0053519 to Pearce et al., which is incorporated herein by reference.

Figure 3:
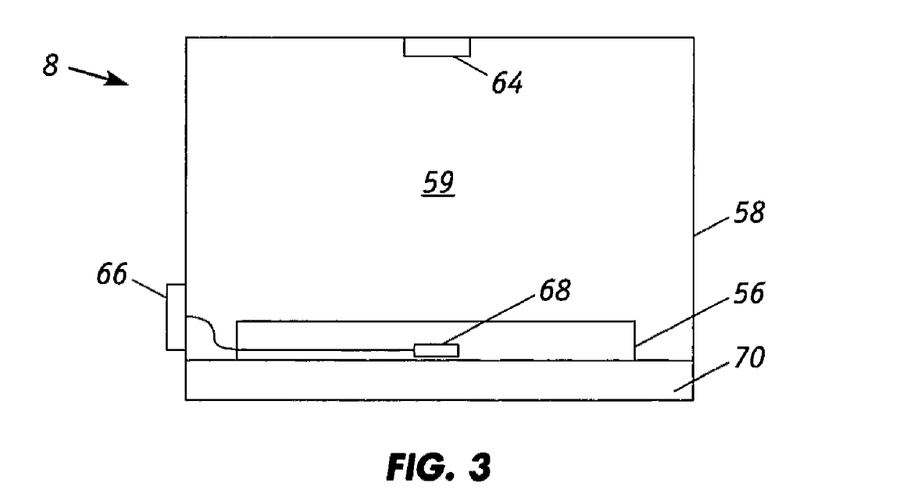
FIG. 3 illustrates an apparatus for cooling the mini-module and taking near infrared radiation (NIR) images of the solar cells therein.

As depicted in FIG. 3, a device 8 for testing mini-modules includes a cooling plate 70 and NIR camera 64 that are positioned within a chamber 59 that is enclosed by housing 58. The temperature within mini-module 56 is monitored with a thermocouple 68 that is embedded in the middle of the encapsulant layer and that is connected to multimeter 66 that displays the temperature. Chamber 59 can be under vacuum in order to limit the level of moisture therein that could otherwise interfere with the quality of the NIR images. In addition, chamber 59 can be darkened to enhance the quality of the images. As the temperature of mini-module 56 is lowered by cold plate 70, NIR images of solar cells in mini-module 56 are simultaneously taken with camera 64. The temperatures at which solar cell failures are detected are also recorded. As the temperature is lowered, induced stress causes one or more materials that form the solar cell to fail and/or the induced stress causes one or more interfaces in the solar cell, especially within the multilayer cell stack, to fail. Interfacial failure between layers of the multilayer cell is often caused by failure of the adhesive layer. The temperature at which the first failure occurs is indicative of the strength of the solar cell; that is, the stronger the solar cell the lower the temperature needed to cause failure. Thus, the test protocol can be employed, for example, to determine which of many different solar cell designs forms the strongest solar cells or to determine which components will form the best solar cells for a given design. As is apparent, different solar cell components such as encapsulant materials can also be tested in this fashion.

The mini-module is particularly suited for quality control to determine whether thin-film solar cells exhibit the requisite structural integrity for incorporation into actual photovoltaic modules with are expected to have a useful life of at least 20 years. In this regard, a preferred thermal protocol is to cool the mini-module containing the solar cells from ambient to a temperature of from about −70° C. to −90° C. and preferably of about −80° C. over a period of time of from about 30 minutes to 120 minutes and preferably from about 45 minutes to 75 minutes. The temperature is preferably lowered at a constant rate. A preferred thermal cycle for solar cells is to cool the mini-module at a constant rate to about −80° C. over a one-hour period and thereafter maintain the mini-module at the lowered temperature for about 10 minutes. A feature of the thermal protocol is that only a single cooling cycle is required and that no heating of the mini-module is necessary. It is expected that monitoring the solar cells for cold-induced failures during this single thermal cycle adequately determines whether the particular solar cells are suitable for commercial applications. The current standard thermal reliability testing protocol for solar cell modules subjects modules to continuous thermal cycling between 90° C. to −40° C. This standard procedure is quite time consuming. The behavior of solar cells to the cold lift-off testing of the present invention can be correlated to the standard thermal reliability testing so as to obviate the need for employing the current standard protocol.

EXAMPLES

Figure 4:
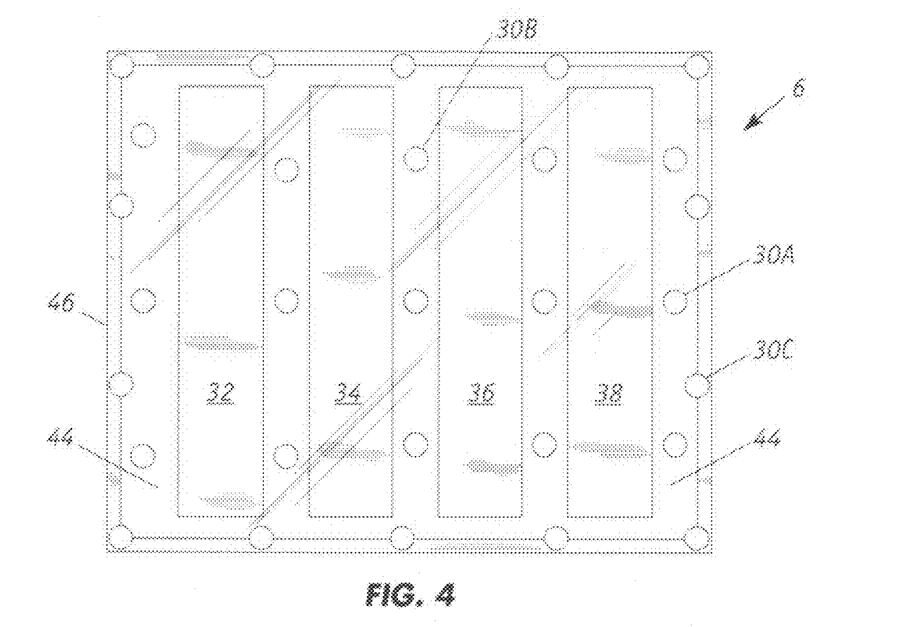
FIG. 4 is a top plan view of another mini-module.

Thin-film solar cells were tested with a mini-module 6 that encased four laminated solar cells 32, 34, 36 and 38 as illustrated in FIG. 4. The construction of mini-module 6 was essentially the same as that of mini-module 4 (FIG. 1B), except that four solar cells are accommodated. Spacers such as 30A, 30B, 30C consisting of 1 mm diameter stainless steel balls were distributed throughout the mini-module between stippled glass upper and lower substrates that were each 8 in. (20.32 cm)×12 in. (30.48 cm) in size. The stippled sides of the glass substrates faced the inside of the mini-module toward the solar cells. Solar edge tape 46 (55 mil thick) from TruSeal Technologies, Inc. (Solon, Ohio) sealed encapsulant 44 within the mini-module. The encapsulant material comprised a polymeric composition commercially available as Z68R7 from Dainippon Ink & Chemicals Ltd. (Tokyo, JP). In forming the laminant layer that encased the solar cells, two layers of the encapsulant material each 24 mil thick were laminated at 170° C. for 5 minutes under vacuum. A K-type thermocouple was embedded in the encapsulant material.

Figure 5:
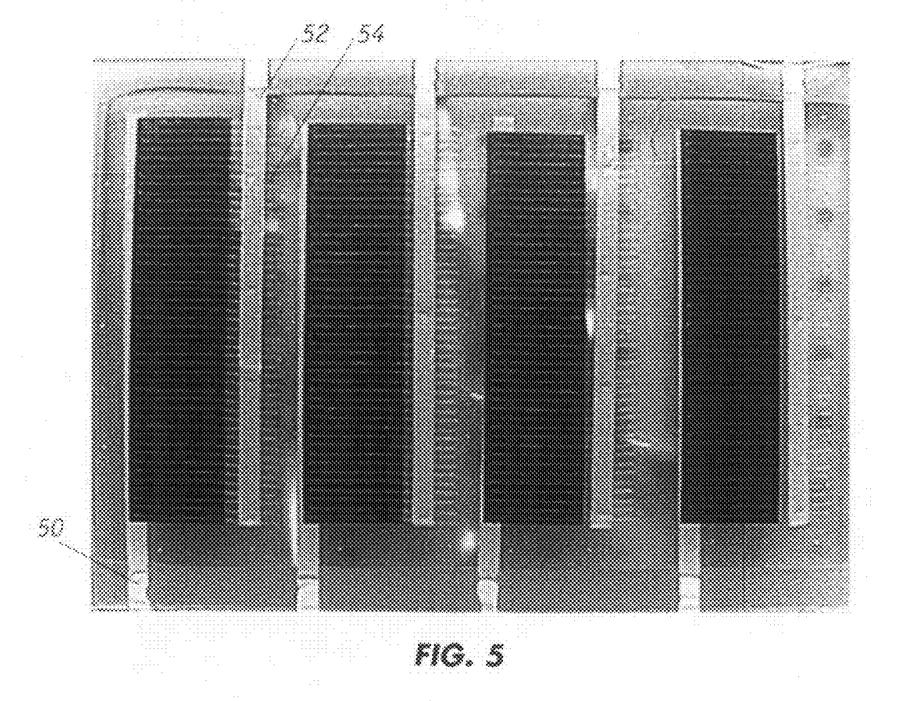
FIG. 5 is a photograph of a mini-module with laminated solar cells formed therein with each solar cell is connected to busbars.

FIG. 5 is an image of a mini-module with four solar cells laminated within the encapsulant material. The dimensions of each of thin-film solar cells are approximately, 156 mm×35 mm×0.050 mm. Conductor wires 54, which are in electrical contact with the top contact layer of each solar cell, are electrically connected to top busbar 52. Specifically, 4-5 points along the length of top busbar 52 were tacked onto conductor wires 54. Bottom busbar 50 is in mechanical contact with the bottom contact layer of the solar cell. Each busbar comprises a nickel-plated conductive ribbon that extends into the exterior of the mini-modular between the glass substrate and the solar edge tape. In this fashion, the electrical characteristics of the solar cells can also be tested, for example, by applying an external voltage across each solar cell.

Figure 6A:
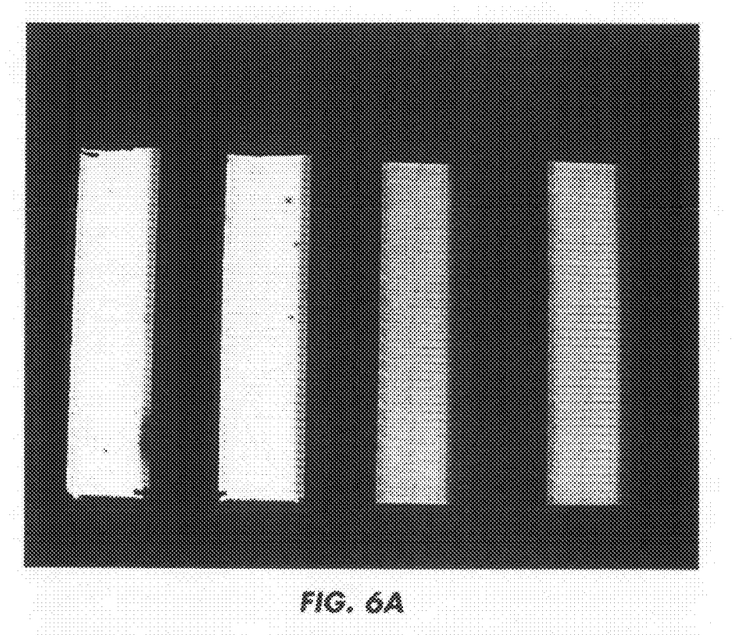
FIGS. 6A and 6B are NIR images of solar cells in a mini-module taken at ambient temperature and at −40° C., respectively.
Figure 6B:
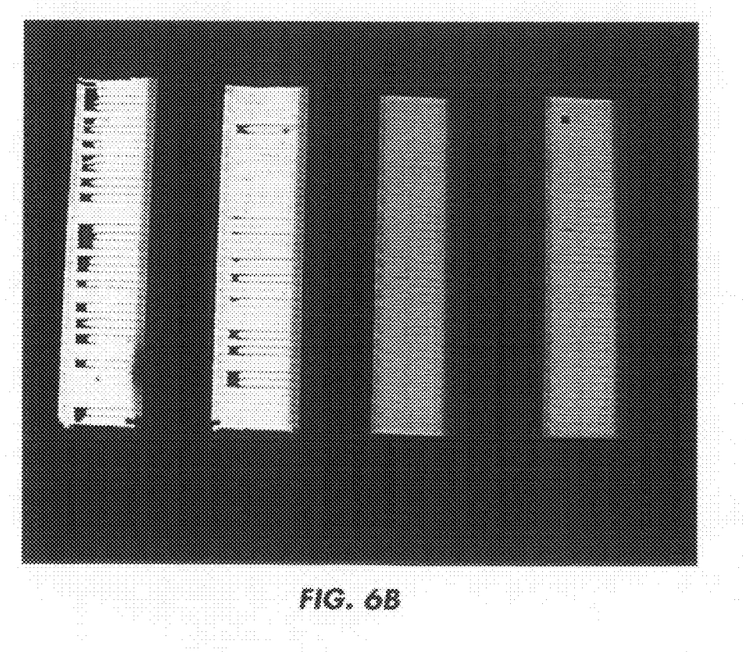

FIG. 6A is an NIR image of four solar cells in a mini-module taken at ambient temperature. FIG. 6B is an NIR image taken of the same mini-module after being cooled to −40° C. The solar cell on the far left side of the mini-module shows significant color changes along the entire length of the solar cell. The second solar cell from the left shows similar patterns of color changes although less pronounced than that of the first solar cell. Two characteristic types of coloration changes in the NIR images of the solar cells are apparent. The first type appears as discrete dark spots or areas. These are evident along the left side of both the first and second solar cells. Each darken area may represent de-lamination of the bottom busbar and/or de-lamination within the multilayer cell stack. The second type appears as one or more dark horizontal lines along the width of the solar cell. Both the first and second solar cells exhibit horizontal line colorations across their entire lengths. This pattern of horizontal lines may be caused by the failure of conductor wires 54 (FIG. 5). For both types of coloration changes, the size and darkness of the color changes correspond to the severity of the failures. Except for a dark area at the top of the fourth solar cell, NIR images of the third and fourth solar cells show no color changes.

Figure 7A:
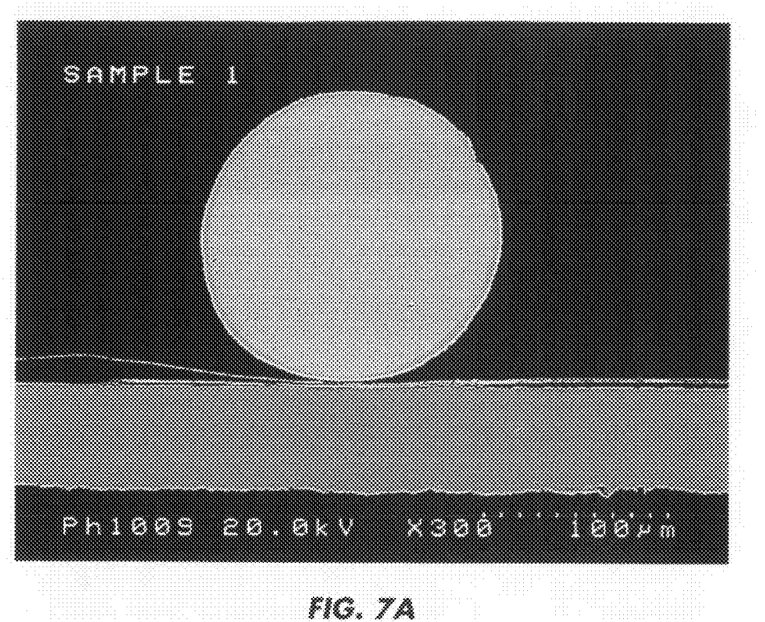
Figure 7B:
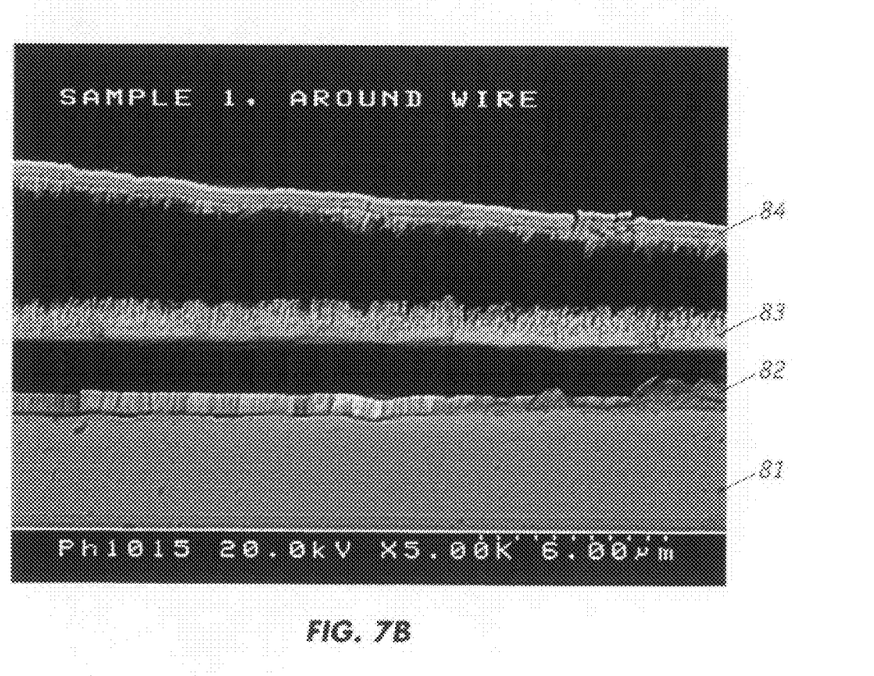

FIG. 7A is an SEM of a cross section of a solar cell at a location where NIR imaging detected a failure. The image shows a conductor wire that is in electrical contact with top contact layer of the solar cell. FIG. 7B is a higher resolution SEM in the same region showing the solar cell substrate layer 81, molybdenum bottom conductor layer 82, CIGS layer 83 and conductor top layer 84. The presence of rough edges on the upper surface of CIGS layer 83 and on the lower surface of conductor top layer 84 suggests that de-lamination occurred between these two layers.

Figure 8A:
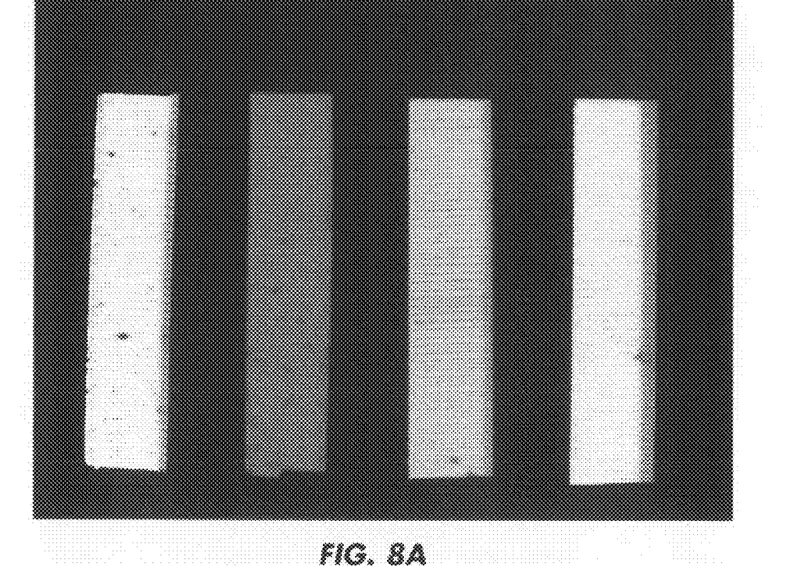
FIGS. 8A and 8B are NIR images of solar cells in a mini-module taken at ambient temperature and at −90° C., respectively.
Figure 8B:
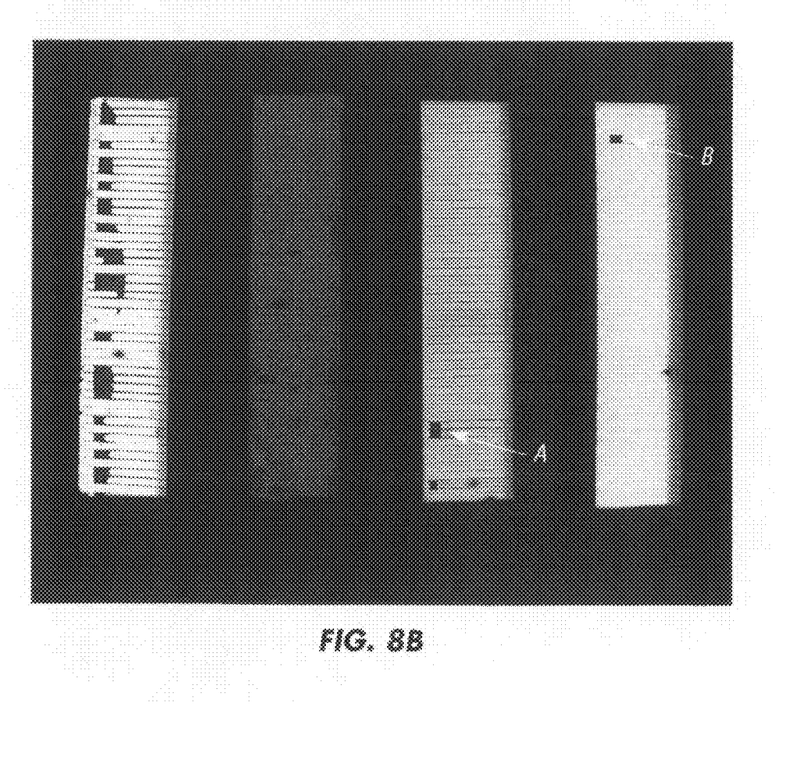

FIG. 8A is an NIR image of another four solar cells in a mini-module taken at ambient temperature and FIG. 8B is an NIR image that was taken of the same mini-module after being cooled to −90° C. The solar cell on the far left side shows significant color changes along its entire length exhibiting darks areas as well as dark horizontal lines. The initial failure was detected by NIR images at −36° C. The second solar cell from the left shows no detectable color changes even at −90° C.; moreover, no color changes were visible to the unaided eye. The third solar cell shows some color changes indicating failures; the initial failure was detected at location A at a temperature between −78 and −80° C. Finally, the fourth solar cell also showed some color changes indicating failures; the initial failure was detected at location B at a temperature of −80° C.

Figure 9A:
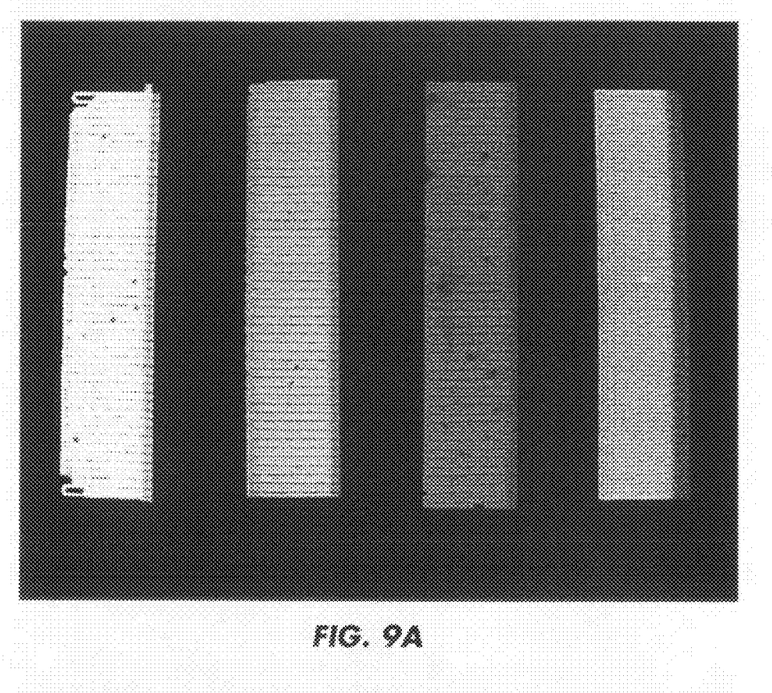
FIGS. 9A and 9B are NIR images of solar cells in a mini-module taken at ambient temperature and at −90° C., respectively.
Figure 9B:
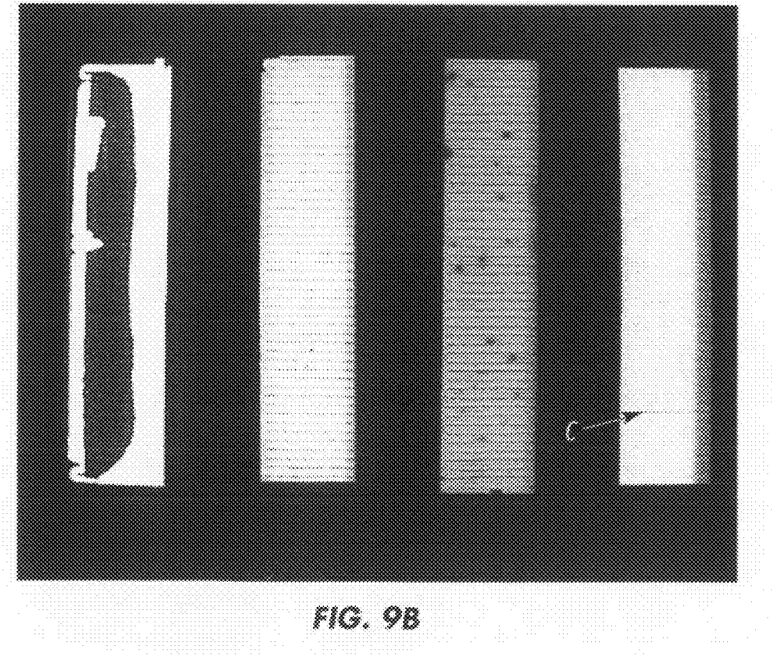

FIG. 9A is an NIR image of another four solar cells in a mini-module taken at ambient temperature and FIG. 9B is an NIR image that was taken of the same mini-module after being cooled to −90° C. The solar cell on the far left side shows significant color changes along its entire length exhibiting a darken area that covers approximately half the solar cell. The initial failure was detected by NIR images at −20° C. The second solar cell from the left shows characteristic dark horizontal lines along its entire length; in addition, some visible changes were also observed at −80° C. The third solar cell shows some darken areas throughout the solar cell but no visible color changes were observed. The fourth solar cell shows a dark horizontal line at location C; no visible color changes were observed.

Finally, solar cells were laminated in mini-modules that were fabricating using 0.7 mm diameter steel balls as spacers (instead of 1.0 mm) along with a correspondingly shorter solar edge tape and less encapsulant material. When these mini-modules were cooled, NIR imaging showed that failures in the solar cells occurred at higher temperatures than when comparable solar cells having the same defects were tested in mini-modules with the larger diameter spacers. In other words, with the smaller spacers less cooling was required to induce failure. One possible explanation is that since there was less encapsulant material laminating the solar cells in the mini-modules with the smaller spacers, the internal temperature of the laminant and solar cell decreased at a faster rate and therefore contracted at a faster rate.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method of testing a solar cell that comprises the steps of:
    positioning the solar cell within a chamber having defined inner dimensions;
    laminating the solar cell with an encapsulant that is added to the chamber;
    cooling the laminated solar cell to a temperature sufficient to cause defects to appear wherein the inner dimensions of the chamber, at least along an axis that is perpendicular to a plane defined by the solar cell, remain substantially constant during cooling; and
    detecting the presence of defects in the solar cell.

2. The method of claim 1 wherein the laminated solar cell is cooled to about −80° C. in less than about 2 hours.

3. The method of claim 2 further comprising the step of maintaining the laminated solar cell at the predetermined temperature for at least about 10 minutes.

4. The method of claim 1 further comprising the step of noting the temperature at which the first defect is detected.

5. The method of claim 1 wherein the step of detecting the presence of defects employs infrared thermography.

6. The method of claim 1 wherein the solar cell is electrically connected to a busbar.

* * * * *